(12) United States Patent
Matsumoto et al.

(10) Patent No.: US 8,501,822 B2
(45) Date of Patent: Aug. 6, 2013

(54) OPHTHALMIC COMPOSITION CONTAINING ALGINIC ACID OR SALT THEREOF

(75) Inventors: Eri Matsumoto, Osaka (JP); Yasuko Nishina, Osaka (JP); Kenichi Haruna, Osaka (JP); Harumasa Arita, Osaka (JP); Akiko Kita, Osaka (JP)

(73) Assignee: Rohto Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/431,002

(22) Filed: Mar. 27, 2012

(65) Prior Publication Data

US 2012/0238519 A1    Sep. 20, 2012

Related U.S. Application Data

(62) Division of application No. 12/305,882, filed as application No. PCT/JP2007/063050 on Jun. 28, 2007.

(30) Foreign Application Priority Data

Jun. 28, 2006    (JP) .................................. 2006-178838
Jul. 5, 2006     (JP) .................................. 2006-186130

(51) Int. Cl.
*A61K 47/00*    (2006.01)

(52) U.S. Cl.
USPC ................ 514/779; 514/777; 514/782

(58) Field of Classification Search
USPC .......................................... 514/777, 779, 782
See application file for complete search history.

(56) References Cited

U.S. PATENT DOCUMENTS

| 4,939,135 | A |   | 7/1990 | Robertson et al. |
| 5,587,175 | A | * | 12/1996 | Viegas et al. ................. 424/427 |
| 2007/0212420 | A1 | * | 9/2007 | Xia et al. ...................... 424/488 |

FOREIGN PATENT DOCUMENTS

| JP | 60-84225    | 5/1985  |
| JP | 1-238530    | 9/1989  |
| JP | 8-502761    | 3/1996  |
| JP | 2002-332248 | 11/2002 |

OTHER PUBLICATIONS

International Search Report for PCT/JP2007/063050, dated Aug. 14, 2007.

* cited by examiner

*Primary Examiner* — Gigi Huang
(74) *Attorney, Agent, or Firm* — Roylance, Abrams, Berdo & Goodman, L.L.P.

(57) ABSTRACT

An ophthalmic composition that, despite containing alginic acid and/or a salt thereof, has improved tackiness during use and provides a satisfactory use feeling. The composition has an improved ability to remain on the eye mucosa. The ophthalmic composition contains (A) alginic acid and/or a salt thereof in combination with (B) hyaluronic acid and/or a salt thereof.

2 Claims, 2 Drawing Sheets

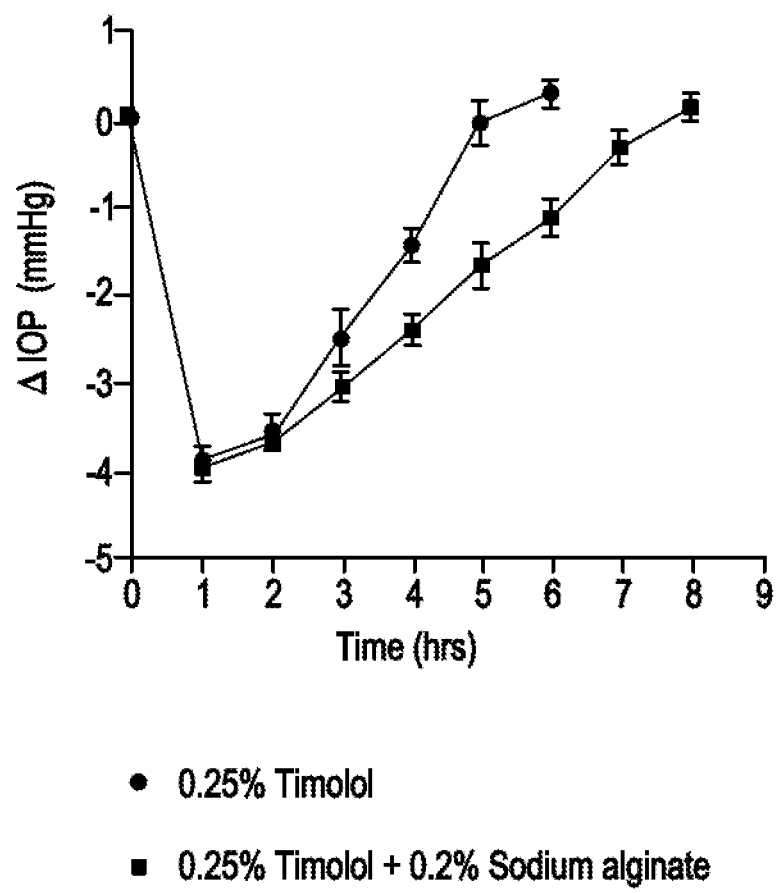

US 8,501,822 B2

OPHTHALMIC COMPOSITION CONTAINING ALGINIC ACID OR SALT THEREOF

TECHNICAL FIELD

The present invention relates to an ophthalmic composition comprising alginic acid and/or a salt thereof, and having satisfactory sense of use and improved retention on an ocular mucosa. The present invention also relates to a method for improving the retention of an ophthalmic composition comprising alginic acid and/or a salt thereof on an ocular mucosa. Furthermore, the present invention relates to a method for reducing the adsorption of alginic acid and/or a salt thereof to a soft contact lens.

BACKGROUND ART

Alginic acid has an action of becoming more viscous after being partially cross-linked with a divalent or higher valent cation such as a $Ca^{2+}$ ion; it is already known that alginic acid can be used as a component in ophthalmic compositions such as eye drops or eye washes (see, for example, Patent Document 1). It has also been discovered that when an ophthalmic composition comprising alginic acid is applied to an eye, $Ca^{2+}$ ions existing on an ocular mucosa or in tear fluid are contacted with alginic acid and make the composition more viscous on the ocular mucosa, and are therefore useful for improving the retention of the composition on the ocular mucosa and maintaining the effects produced by active ingredients. The ophthalmic compositions comprising alginic acid, however, become disadvantageously sticky during use; it is desirable to solve this disadvantage to produce a better sense of use. The effect of alginic acid on soft contact lenses (hereinafter referred to as an "SCL") has, to date, not yet been studied in detail. The present inventors repeated the research for SCL ophthalmic compositions comprising alginic acid, and confirmed that there is fear of adsorption to an SCL in the SCL ophthalmic compositions comprising alginic acid alone. In particular, when the fit of a contact lens (the compatibility of a contact lens design with the base curve of a user's cornea) is poor, the adsorption of alginic acid to an SCL may cause discomfort or the feeling of an uncomfortable foreign body when the SCL is used; when alginic acid is mixed with an SCL ophthalmic composition, it is important to suppress the adsorption of alginic acid to the SCL.

On the other hand, it is known that hyaluronic acid is a linear polymeric polysaccharide in which D-glucuronic acid and N-acetyl-D-glucosamine bond with each other, and that it has high viscosity and a high water-holding ability. It has also been reported in the ophthalmic field that the use of hyaluronic acid is effective for promoting the extension of a corneal epithelium, treating dry-eye, and the like (see, for example, Patent Documents 2 and 3). Further, it is believed that hyaluronic acid is particularly effective for frequent inflammation sufferers such as contact lens users and patients suffering from dry-eye because hyaluronic acid has a radical-scavenging effect, and is useful for body defense at inflammatory sites. The effect hyaluronic acid has on the sense of use of an ophthalmic composition comprising alginic acid, the retention of an ophthalmic composition comprising alginic acid on an ocular mucosa, the adsorption of alginic acid to an SCL and the like is unknown.

Patent Document 1: Japanese Patent Application Laid-Open Publication No. 2002-332248
Patent Document 2: Japanese Patent Application Laid-Open Publication No. 1989-238530
Patent Document 3: Japanese Patent Application Laid-Open Publication No. 1985-84225

DISCLOSURE OF THE INVENTION

Problems to be Solved by the Invention

The main object of the present invention is to provide an ophthalmic composition in which stickiness during use and the like, and retention on an ocular mucosa are both improved, despite comprising alginic acid and/or a salt thereof. Furthermore, the main object of the present invention is to provide an ophthalmic composition in which the adsorption of alginic acid and/or a salt thereof to an SCL is reduced.

Means for Solving the Problems

As a result of intensive studies for solving the above-described problem, the present inventors found that by mixing Component (B) hyaluronic acid and/or a salt thereof with an ophthalmic composition comprising Component (A) alginic acid and/or a salt thereof, stickiness during use and the like can be improved to exert a satisfactory sense of use, and the retention on an ocular mucosa can be improved.

As a result of further studies for an ophthalmic composition comprising alginic acid, the present inventors found that in an ophthalmic composition that comprises alginic acid and/or a salt thereof alone, alginic acid and/or a salt thereof adsorbs to an SCL, whereas in an ophthalmic composition that comprises Component (B), i.e., hyaluronic acid and/or a salt thereof together with Component (A), i.e., alginic acid and/or a salt thereof, the adsorption of alginic acid and/or a salt thereof to an SCL can be suppressed. The present invention has been completed by making further improvements based on these findings.

Specifically, the present invention provides the following ophthalmic compositions:

Item 1-1: An ophthalmic composition comprising Component (A) at least one member selected from the group consisting of alginic acid and salts thereof, and Component (B) at lease one member selected from the group consisting of hyaluronic acid and salts thereof.

Item 1-2: The ophthalmic composition according to Item 1-1, which contains Component (B) in a ratio of 0.3 to 6,000 parts by weight per 100 parts by weight of Component (A).

Item 1-3: The ophthalmic composition according to Item 1-1, which contains Component (A) in a total amount of 0.001 to 5% by weight based on a total weight of the ophthalmic composition.

Item 1-4: The ophthalmic composition according to Item 1-1, which contains Component (B) in a total amount of 0.0001 to 2% by weight based on the total weight of the ophthalmic composition.

Item 1-5: The ophthalmic composition according to Item 1-1, which is an eye drop, an eye wash, or a wetting and rewetting drop for a contact lens.

Item 1-6: The ophthalmic composition according to Item 1-1, which is an ophthalmic composition for an SCL.

Item 1-7: The ophthalmic composition according to Item 1-1, which further comprises a pharmacologically active ingredient.

The present invention also provides the following methods for improving the retention of an ophthalmic composition on an ocular mucosa:

Item 2-1: A method for improving the retention of an ophthalmic composition on an ocular mucosa, which comprises the step of mixing Component (B) at least one member selected from the group consisting of hyaluronic acid and salts thereof with an ophthalmic composition that contains Component (A) at least one member selected from the group consisting of alginic acid and salts thereof.

Item 2-2: The method according to Item 2-1, wherein Component (B) is mixed at a ratio of 0.3 to 6,000 parts by weight per 100 parts by weight of Component (A).

Item 2-3: The method according to Item 2-1, wherein Component (A) is contained in a total amount of 0.001 to 5% by weight based on a total weight of the ophthalmic composition.

Item 2-4: The method according to Item 2-1, wherein Component (B) is mixed in a total amount of 0.0001 to 2% by weight based on a total weight of the ophthalmic composition.

Item 2-5: The method according to Item 2-1, wherein the ophthalmic composition is an eye drop, an eye wash, or a wetting and rewetting drop for a contact lens.

Item 2-6: The method according to Item 2-1, wherein the ophthalmic composition is an ophthalmic composition for an SCL.

Item 2-7: The method according to Item 2-1, wherein the ophthalmic composition further comprises a pharmacologically active ingredient.

The present invention further provides the following methods for reducing the adsorption of alginic acid and/or a salt thereof to an SCL:

Item 3-1: A method for reducing the adsorption, to an SCL, of at least one member selected from the group consisting of alginic acid and salts thereof, which comprises the step of incorporating Component (B) at least one member selected from the group consisting of hyaluronic acid and salts thereof with an SCL ophthalmic composition that contains Component (A) at least one member selected from the group consisting of alginic acid and salts thereof.

Item 3-2: The method according to Item 3-1, wherein Component (B) is mixed at a ratio of 0.3 to 6,000 parts by weight per 100 parts by weight of Component (A).

Item 3-3: The method according to Item 3-1, wherein Component (A) is contained in a total amount of 0.001 to 5% by weight based on a total weight of the SCL ophthalmic composition.

Item 3-4: The method according to Item 3-1, wherein Component (B) is mixed in a total amount of 0.0001 to 2% by weight based on a total weight of the SCL ophthalmic composition.

Item 3-5: The method according to Item 3-1, wherein the SCL ophthalmic composition is an SCL eye drop, an SCL eye wash, or an SCL wetting and rewetting drop.

Item 3-6: The method according to Item 3-1, wherein the SCL ophthalmic composition further comprises a pharmacologically active ingredient.

The present invention still further provides the following methods for suppressing the adsorption of alginic acid and/or a salt thereof to an SCL:

Item 4-1: A method for suppressing the adsorption, to an SCL, of at least one member selected from the group consisting of alginic acid and salts thereof, which comprises the step of contacting an ophthalmic composition comprising Component (A) at least one member selected from the group consisting of alginic acid and salts thereof and Component (B) at least one member selected from the group consisting of hyaluronic acid and salts thereof, with an SCL.

Item 4-2: The method according to Item 4-1, which is a method for suppressing the adsorption, to an SCL, of at least one member selected from the group consisting of alginic acid and salts thereof during the administration of an eye drop or the washing an eye, which comprises the step of applying the ophthalmic composition of Item 1-6 to an eye wearing an SCL.

Item 4-3: The method according to Item 4-1, wherein Component (B) is contained at a ratio of 0.3 to 6,000 parts by weight per 100 parts by weight of Component (A) in the ophthalmic composition.

Item 4-4: The method according to Item 4-1, wherein Component (A) is contained in a total amount of 0.001 to 5% by weight based on a total weight of the ophthalmic composition.

Item 4-5: The method according to Item 4-1, wherein Component (B) is contained in a total amount of 0.0001 to 2% by weight based on a total weight of the ophthalmic composition.

Item 4-6: The method according to Item 4-1, wherein the ophthalmic composition is an eye drop for an SCL, an eye wash for an SCL, or a wetting and rewetting drop for an SCL.

Item 4-7: The method according to Item 4-1, wherein the ophthalmic composition further comprises a pharmacologically active ingredient.

The present invention still further provides the following methods for retaining an ophthalmic composition on an ocular mucosa:

Item 5-1: A method for retaining an ophthalmic composition on an ocular mucosa, which comprises the step of applying an ophthalmic composition containing Component (A) at least one member selected from the group consisting of alginic acid and salts thereof, and Component (B) at least one member selected from the group consisting of hyaluronic acid and salts thereof to an eye.

Item 5-2: The method according to Item 5-1, wherein Component (B) is contained at a ratio of 0.3 to 6,000 parts by weight per 100 parts by weight of Component (A) in the ophthalmic composition.

Item 5-3: The method according to Item 5-1, wherein Component (A) is contained in a total amount of 0.001 to 5% by weight based on a total weight of the ophthalmic composition.

Item 5-4: The method according to Item 5-1, wherein Component (B) is contained in a total amount of 0.0001 to 2% by weight based on a total weight of the ophthalmic composition.

Item 5-5: The method according to Item 5-1, wherein the ophthalmic composition is an eye drop, an eye wash, or a wetting and rewetting drop for a contact lens.

Item 5-6: The method according to Item 5-1, wherein the ophthalmic composition is an ophthalmic composition for an SCL.

Item 5-7: The method according to Item 5-1, wherein the ophthalmic composition further comprises a pharmacologically active ingredient.

The present invention still further provides the following uses:

Item 6-1: The use of Component (A) at least one member selected from the group consisting of alginic acid and salts thereof, and Component (B) at least one member selected from the group consisting of hyaluronic acid and salts thereof for the manufacture of an ophthalmic composition.

Item 6-2: The use according to Item 6-1, wherein Component (B) is contained at a ratio of 0.3 to 6,000 parts by weight per 100 parts by weight of Component (A) in the ophthalmic composition.

Item 6-3: The use according to Item 6-1, wherein Component (A) is contained in a total amount of 0.001 to 5% by weight based on a total weight of the ophthalmic composition.

Item 6-4: The use according to Item 6-1, wherein Component (B) is contained in a total amount of 0.0001 to 2% by weight based on a total weight of the ophthalmic composition.

Item 6-5: The use according to Item 6-1, wherein the ophthalmic composition is an eye drop, an eye wash, or a wetting and rewetting drop for a contact lens.

Item 6-6: The use according to Item 6-1, wherein the ophthalmic composition is an ophthalmic composition for an SCL.

Item 6-7: The use according to Item 6-1, wherein the ophthalmic composition further comprises a pharmacologically active ingredient.

Item 7-1: The use of Component (B) at least one member selected from the group consisting of hyaluronic acid and salts thereof for the manufacture of an ophthalmic composition containing Component (A) at least one member selected from the group consisting of alginic acid and salts thereof, the ophthalmic composition having improved retention of at least one member selected from the group consisting of alginic acid and salts thereof.

Item 7-2: The use according to Item 7-1, wherein Component (B) is used at the ratio of 0.3 to 6,000 parts by weight per 100 parts by weight of Component (A) in the ophthalmic composition.

Item 7-3: The use according to Item 7-1, wherein Component (A) is contained in a total amount of 0.001 to 5% by weight based on a total weight of the ophthalmic composition.

Item 7-4: The use according to Item 7-1, wherein Component (B) is used in a total amount of 0.0001 to 2% by weight based on a total amount of the ophthalmic composition.

Item 7-5: The use according to Item 7-1, wherein the ophthalmic composition is an eye drop, an eye wash, or a wetting and rewetting drop for a contact lens.

Item 7-6: The use according to Item 7-1, wherein the ophthalmic composition is an ophthalmic composition for an SCL.

Item 7-7: The use according to Item 7-1, wherein the ophthalmic composition further comprises a pharmacologically active ingredient.

Item 8-1: The use of Component (B) at least one member selected from the group consisting of hyaluronic acid and salts thereof for the manufacture of an ophthalmic composition containing Component (A) at least one member selected from the group consisting of alginic acid and salts thereof, the ophthalmic composition having the suppressed adsorption of at least one member selected from the group consisting of alginic acid and salts thereof to an SCL.

Item 8-2: The use according to Item 8-1, wherein Component (B) is used at a ratio of 0.3 to 6,000 parts by weight per 100 parts by weight of Component (A) in the ophthalmic composition.

Item 8-3: The use according to Item 8-1, wherein Component (A) is contained in a total amount of 0.001 to 5% by weight based on a total weight of the ophthalmic composition.

Item 8-4: The use according to Item 8-1, wherein Component (B) is used in a total amount of 0.0001 to 2% by weight based on a total weight of the ophthalmic composition.

Item 8-5: The use according to Item 8-1, wherein the ophthalmic composition is an eye drop, an eye wash, or a wetting and rewetting drop for a contact lens.

Item 8-6: The use according to Item 8-1, wherein the ophthalmic composition is an ophthalmic composition for an SCL.

Item 8-7: The use according to Item 8-1, wherein the ophthalmic composition further comprises a pharmacologically active ingredient.

Effects of the Invention

The ophthalmic composition of the present invention has a reduced stickiness during use and this results in an improved sense of use compared to an ophthalmic composition comprising alginic acid and/or a salt thereof alone. Such distinguished effects of the present invention can be achieved by using Component (B) hyaluronic acid and/or a salt thereof in combination with Component (A) alginic acid and/or a salt thereof. The ophthalmic composition of the present invention less causes blurred vision and the like than an ophthalmic composition comprising hyaluronic acid and/or a salt thereof alone. Because dry eye sufferers and contact lens users tend to be easily affected by problems caused by the stickiness of an ophthalmic composition and blurred vision, the ophthalmic composition of the present invention is particularly useful for dry eye sufferers and contact lens users.

The ophthalmic composition of the present invention has an improved retention on an ocular mucosa. Specifically, the ophthalmic composition of the present invention exhibits a longer retention of mixed components, such as hyaluronic acid and/or a salt thereof, and other pharmacologically active ingredients, on an ocular mucosa. This increases the retentivity of the useful effects produced therefrom. Because such improved retention of the pharmacologically active ingredients on an ocular mucosa is effective for the alleviation or amelioration of symptoms, such as corneal drying and inflammation, which often occur in contact lens users, the ophthalmic composition of the present invention is useful as an ophthalmic composition for an SCL. Furthermore, when the ophthalmic composition of the present invention is used as an ophthalmic composition for an SCL, by pre-contacting an SCL with the ophthalmic composition and applying, or by putting an SCL immediately after applying the ophthalmic composition or washing an eye with the ophthalmic composition, the retention of the ophthalmic composition on an ocular mucosa can be improved. The above-described effects can be thus more effectively obtained.

Furthermore, in the ophthalmic composition of the present invention, the adsorption of alginic acid and/or a salt thereof to an SCL is suppressed; therefore, the ophthalmic composition is highly useful as an SCL wetting and rewetting drop, or as an ophthalmic composition such as an eye drop or an eye wash used when wearing an SCL.

BEST MODE FOR CARRYING OUT THE INVENTION (I) Ophthalmic Composition

The ophthalmic composition of the present invention comprises (A) at least one member selected from the group consisting of alginic acid and salts thereof (which may be simply referred to as Component (A) herein).

The alginic acid is a polysaccharide composed of mannuronic acid (which may be simply referred to as "M" hereinafter) and guluronic acid (which may be simply referred to as "G" hereinafter), and is a block copolymer in which homopolymer fractions of mannuronic acid (MM fractions), homopolymer fractions of guluronic acid (GG fractions) and fractions of randomly arranged mannuronic acid and guluronic acid (MG fractions) are randomly bonded.

The origin of the alginic acid used in the present invention is not particularly limited. For example, alginic acid derived from alga such as alga from the *Lessonia* genus (for example, *Lessonia nigrescens*) and alga from the *Laminaria* genus (for example, *Laminaria japonica*) may be used.

For the alginic acid used in the present invention, the composition ratio of mannuronic acid to guluronic acid (M/G ratio; molar ratio) is not particularly limited. For example, alginic acid with an M/G ratio ranging from 0.4 to 4.0 is widely used. The smaller the M/G ratio, the greater the improvement in the retention of the composition. Therefore, it is desirable that the M/G ratio be 2.5 or less, preferably 2.0 or less, more preferably 1.6 or less, from the viewpoint of improved retention of other pharmacologically active ingredients mixed on application sites. In particular, it is desirable to use alginic acid having an M/G ratio ranging preferably from 0.4 to 2.0, more preferably from 0.5 to 1.6, particularly preferably from 1.0 to 1.6. In the present invention, the M/G ratio is a value calculated by dividing alginic acid into block units, fractionating them, and quantifying each of them; the ratio is specifically determined in accordance with the method as described in A. Haug et al., Carbohyd. Res. 32 (1974), p. 217-225.

In the alginic acid used in the present invention, the ratio of the MM fraction, the GG fraction and the MG fraction is not particularly limited, and may be appropriately selected depending on the application or form of the ophthalmic composition.

In the present invention, a low- to high-molecular weight alginic acid can be appropriately used.

The salts of the alginic acid are not specifically limited, so long as they are pharmacologically or physiologically acceptable. Specific examples of the alginic acid salt include sodium salt, potassium salt, triethanol amine salt, ammonium salt, and the like. The alginic acid salt may be used alone or in any combination of two or more types thereof.

In the ophthalmic composition of the present invention, a single type of alginic acid and salts thereof may be used, or any combination of two or more types thereof may be used. In particular, alginic acid, sodium alginate and potassium alginate are preferably used in the present invention because they are water-soluble.

Alginic acid and salts thereof are commercially available from Kibun Food Chemifa Co., Ltd., Kimica Corporation, Fuji Chemical Industry Co., Ltd., Kelco Corporation (UK), Sigma (US), PRONOVA Biopolymer Ltd. (NO), and the like; these commercial products can be used in the present invention.

The proportion of Component (A) in the ophthalmic composition of the present invention is not particularly limited, and it can be appropriately selected depending on the types of Component (A), and the application or form of the composition. One example of the proportion of Component (A), the total amount of Component (A) in the ophthalmic composition is from 0.001 to 5% by weight, preferably from 0.001 to 1% by weight, more preferably from 0.001 to 0.5% by weight. For example, when the ophthalmic composition is an eye drop or a wetting and rewetting drop for a contact lens, its amount is more preferably from 0.001 to 0.5% by weight, particularly preferably from 0.005 to 0.2% by weight; when the ophthalmic composition is an eye wash, its amount is more preferably from 0.001 to 0.2% by weight, particularly preferably from 0.005 to 0.1% by weight. By selecting Component (A) within the above-described concentration range, it is possible to improve the retention of the ophthalmic composition to obtain a better sense of use. The ophthalmic composition of the present invention comprises (B) at least one member selected from the group consisting of hyaluronic acid and salts thereof (which may be simply referred to as Component (B) herein) in addition to Component (A). By adding Component (B), it is possible to change the gelation property provided by Component (A) to reduce the stickiness of the ophthalmic composition during use and to produce a better sense of use, as well as improve the retention on an ocular mucosa. Furthermore, Component (B) enables the suppression of the adsorption of Component (A) to an SCL.

Component (B), i.e., hyaluronic acid and a salt thereof, is a mucopolysaccharide polymeric compound that exerts a moisturizing action on an ocular mucosa and the like. The origins of hyaluronic acid and a salt thereof used in the present invention are not particularly limited; they may, for example, be derived from cock's comb or obtained from microorganisms. The average molecular weight of the hyaluronic acid used in the present invention is not particularly limited; for example, it may be in the range of from 1,000 to 5,000,000, preferably from 200,000 to 4,000,000, more preferably from 600,000 to 2,500,000, and particularly preferably from 800,000 to 2,000,000. Herein, the average molecular weight of the hyaluronic acid describes a viscosity average molecular weight. The viscosity average molecular weight can be measured by a known method for measuring. Specifically, hyaluronic acid and/or a salt thereof (dry matter) is dissolved in a 0.2 M sodium chloride solution, the intrinsic viscosity ($\eta$) is determined at 30° C., and the viscosity average molecular weight is calculated according to Laurent's formula ($\eta$(intrinsic viscosity)=0.00036×Mv (viscosity average molecular weight)$^{0.78}$). The intrinsic viscosity ($\eta$) is determined in accordance with the Japanese Pharmacopoeia Fourteenth Edition, General Test Procedures, Viscometry (Capillary Viscometer Method).

Examples of the hyaluronic acid salt include salts with an alkali metal, such as sodium or potassium; salts with an alkaline earth metal, such as calcium or magnesium; and salts with a metal, such as aluminum. Sodium salts and potassium salts are preferable as such salts; sodium salts are more preferable. It is preferable to use hyaluronic acid salts because they are more stable than hyaluronic acid.

Commercially available hyaluronic acid and salts thereof can be used in the present invention. Typical commercial products include "Sodium Biohyaluronate" (trade name; produced by Shiseido Co., Ltd.), "Hyaluronsan HA-QA" (trade name; produced by Q.P. Corporation), "Hyaluronsan HA-AM" (trade name; produced by Q.P. Corporation) and the like.

The proportion of Component (B) in the ophthalmic composition of the present invention is not particularly limited, and it can be appropriately selected depending on the types of Component (A) and Component (B), the mixing ratio of Component (A) and Component (B), and the application and form of the composition. As one example of the proportion of Component (B), the total amount of Component (B) may be from 0.0001 to 2% by weight, preferably from 0.001 to 0.3% by weight in the ophthalmic composition. For example, when the ophthalmic composition is an eye drop or a wetting and rewetting drop for a contact lens, its amount may be more preferably from 0.002 to 0.3% by weight, particularly preferably from 0.01 to 0.1% by weight; when the ophthalmic composition is an eye wash, it may be more preferably from 0.001 to 0.1% by weight, particularly preferably from 0.001 to 0.05% by weight.

In order to more effectively achieve the improvement in the sense of use and the retention of the ophthalmic composition of the present invention, and the suppression of the adsorption of Component (A) to an SCL, it is desirable that the mixing ratio of Component (A) and Component (B) each satisfy the following. That is, the total amount of Component (B) is from 0.3 to 6,000 parts by weight, preferably from 0.5 to 3,000 parts by weight, more preferably from 1 to 1,000 parts by weight, particularly preferably from 10 to 200 parts by weight, and further particularly preferably from 30 to 200 parts by weight, per 100 parts by weight of total weight of Component (A).

Preferably, the ophthalmic composition of the present invention further comprises a buffer agent. The buffer agents that can be mixed with the ophthalmic composition of the present invention are not particularly limited, so long as they are pharmacologically or physiologically acceptable. Examples of the buffer agent include boric acid buffer agents, phosphoric acid buffer agents, carbonic acid buffer agents, citric acid buffer agents, acetic acid buffer agents, and epsilon-aminocaproic acid. These buffer agents may be used in combination. Preferable buffer agents include boric acid buffer agents, phosphoric acid buffer agents, carbonic acid buffer agents and citric acid buffer agents. Particularly preferable buffer agents are boric acid buffer agents, citric acid buffer agents and phosphoric acid buffer agents. Examples of boric acid buffer agents include salts of boric acid, such as alkali metal salts of boric acid and alkaline earth metal salts of boric acid. Examples of phosphoric acid buffer agents include salts of phosphoric acid, such as alkali metal salts of phosphoric acid and alkaline earth metal salts of phosphoric acid. Examples of citric acid buffer agents include alkali metal salts of citric acid and alkaline earth metal salts of citric acid. Hydrates of salts of boric acid and salts of phosphoric acid may be used as the boric acid buffer agent and phosphoric acid buffer agent, respectively. More specifically, examples include boric acid or a salt thereof (sodium borate, potassium tetraborate, potassium metaborate, ammonium borate, borax, or the like); phosphoric acid or a salt thereof (disodium hydrogen phosphate, sodium dihydrogen phosphate, potassium dihydrogen phosphate, trisodium phosphate, dipotassium phosphate, calcium monohydrogen phosphate, calcium dihydrogen phosphate, or the like); carbonic acid or a salt thereof (sodium hydrogen carbonate, sodium carbonate, ammonium carbonate, potassium carbonate, calcium carbonate, potassium hydrogen carbonate, magnesium carbonate, or the like); citric acid or a salt thereof (sodium citrate, potassium citrate, calcium citrate, sodium dihydrogen citrate, disodium citrate, or the like); and acetic acid or a salt thereof (ammonium acetate, potassium acetate, calcium acetate, sodium acetate, or the like). These buffer agents may be used alone or in any combination of two or more types thereof.

When the buffer agent is mixed with in the ophthalmic composition of the present invention, the proportion of the buffer agents depend on the type of the buffer agent used and effects to be achieved, and cannot be uniformly defined. For example, the proportion of the buffer agent in a total amount of the ophthalmic composition may be from 0.001 to 10% by weight, preferably from 0.01 to 5% by weight. More specifically, when a boric acid buffer agent or a phosphoric acid buffer agent is used, the proportion of the buffer agent in the composition may be, for example, from 0.001 to 10% by weight, preferably from 0.01 to 5% by weight; when a carbonic acid buffer agent is used, it may be, for example, from 0.001 to 5% by weight, preferably from 0.005 to 3% by weight; when a citric acid buffer agent is used, it may be, for example, from 0.001 to 5% by weight, preferably from 0.005 to 3% by weight; when an acetic acid buffer agent is used, it may be, for example, from 0.001 to 5% by weight, preferably from 0.005 to 3% by weight; and when epsilon-aminocaproic acid is used, it may be, for example, from 0.005 to 10% by weight, preferably from 0.01 to 5% by weight.

The ophthalmic composition of the present invention is in a liquid or gel form, and preferably is in a liquid form. Ophthalmically acceptable water, preferably purified water or extra-pure water is used as a base of the composition. In a preferable embodiment of the ophthalmic composition of the present invention, an aqueous ophthalmic composition comprising 5% by weight or more, preferably 20% by weight or more, more preferably 50% by weight or more, particularly preferably 90% by weight or more of water, based on the total amount of the composition is desirable.

The pH of the ophthalmic composition of the present invention is not particularly limited, so long as it is within a pharmacologically or physiologically acceptable range. The pH of the ophthalmic composition of the present invention may be, for example, in a range of from 5 to 9, preferably from 5.5 to 8.5, more preferably from 6 to 8. When the pH is within the above-described range, the composition is safe for application to the eyes or lenses, and ophthalmic preparations therefrom can be made available. Additionally, it is possible to further improve the effects of the present invention if the pH is within the above-described range.

Further, the ratio of osmotic pressure of the ophthalmic composition of the present invention may be adjusted to a ratio within a range acceptable for a living body, if necessary. An appropriate ratio of osmotic pressure depends on the application or the form of the composition; generally, it may be from 0.2 to 2.5, preferably from 0.3 to 1.7, more preferably from 0.4 to 1.6, still more preferably from 0.5 to 1.5, particularly preferably from 0.6 to 1.4, further particularly preferably from 0.9 to 1.2. Also, it is possible to further improve the effects of the present invention when the pH is within the above-described range.

In the ophthalmic composition of the present invention, the ratio of osmotic pressure is defined as a ratio of the osmotic pressure of a sample relative to that of a 0.9 w/v % aqueous sodium chloride solution, according to the Japanese Pharmacopoeia Fourteenth Edition; the osmotic pressure is measured in accordance with the method for measuring osmotic pressure (freezing point depression method) as described in the Japanese Pharmacopoeia. A standard solution for measuring a ratio of an osmotic pressure is prepared by drying sodium chloride (the Japanese Pharmacopoeia standard reagent) at 500 to 650° C. for 40 to 50 minutes, allowing it to cool in a desiccator (silica gel), precisely weighing out 0.900 grams thereof, dissolving it in purified water, and precisely adjusting the amount of the solution to 100 mL. Alternatively, a commercially available standard solution for measuring a ratio of an osmotic pressure (0.9 w/v % aqueous sodium chloride-containing solution) may be used.

The pH and the ratio of osmotic pressure can be adjusted by a known method in the art using an inorganic salt, a polyhydric alcohol, a sugar alcohol, a saccharide, or the like.

So long as the effects of the present invention are not impaired, the ophthalmic composition of the present invention can comprise various components (including pharmacologically active components and physiologically active components) in any combination, in addition to the components as described above. As described above, because the ophthalmic composition of the present invention has improved retention on an ocular mucosa, if the pharmacologically active ingredients (pharmacologically active components and physiologically active components) are mixed with the ophthalmic composition of the present invention, improvement of the retention of these components on an ocular mucosa can be expected. Particularly regarding water-soluble pharmacologically active ingredients, further improvement of the retention on the ocular mucosa can be expected. The types of such pharmacologically active ingredients are not particularly limited; for example, active ingredients in various medicines described in Nonprescription Drug Manufacturing (Importing) Approval Standard 2000 Edition (under the supervision of Yakuji Sinsa Kenkyukai (Pharmaceutical Examining Society)) can be listed. Specific components that can be used in ophthalmic drugs are as follows.

Specific components include Epinephrine, epinephrine hydrochloride, ephedrine hydrochloride, tetrahydrozoline hydrochloride, naphazoline hydrochloride, phenylephrine hydrochloride, methylephedrine hydrochloride, naphazoline nitrate, neostigmine methylsulfate, zinc sulfate, zinc lactate, allantoin, epsilon-aminocaproic acid, lysozyme chloride, sodium azulene sulfonate, dipotassium glycyrrhizinate, berberine chloride, berberine sulfate, diphenhydramine hydrochloride, chlorpheniramine maleate, retinol acetate, retinol palmitate, pyridoxine hydrochloride, flavin adenine dinucleotide sodium, cyanocobalamin, panthenol, calcium pantothenate, sodium pantothenate, tocopherol acetate, potassium aspartate, magnesium aspartate, a mixture of magnesium aspartate and potassium aspartate, aminoethylsulfonic acid, sodium chondroitin sulfate, sulfamethoxazole, sulfisoxazole, sulfamethoxazole sodium, sulfisomidine sodium, glucose, hydroxyethyl cellulose, hydroxypropylmethyl cellulose, methyl cellulose, polyvinyl alcohol (completely or partially saponified product), polyvinyl pyrrolidone, and the like.

Further, in order to prepare the ophthalmic composition of the present invention in a desired form, various components and additives can be appropriately selected and mixed singly or in any combination in the ophthalmic composition by a conventional method, as long as the effects of the present invention are not impaired. As the component and the additive, for example, various additives as described in Pharmaceutical Excipients Directory 2005 (edited by Japan Pharmaceutical Excipients Council) are listed. Typical additives are listed as follows.

Listed additives include macrogol, poloxamer, poloxamine, polysorbate 80, POE (60) hardened castor oil, alkyl diaminoethylglycine, benzalkonium chloride, parabens, potassium sorbate, polyhexamethylene biguanide, potassium chloride, sodium chloride, calcium chloride, magnesium sulfate, glycerin, propylene glycol, camphor, geraniol, borneol, menthol, fennel oil, cool mint oil, spearmint oil, peppermint oil, bergamot oil, eucalyptus oil, rose oil, sodium edetate, citric acid, trometamol, and the like.

The ophthalmic composition of the present invention is used in the form of, for example, an eye drop (including an eye drop that can be applied to an eye wearing an SCL), an eye wash (including an eye wash that can be used for an eye wearing an SCL), a wetting and rewetting drop for an SCL, a care solution for an SCL (a disinfecting solution for an SCL, a storage solution for an SCL, a washing solution for an SCL, and a washing and storage solution for an SCL), or the like. Of these, eye drops and eye washes are preferable; eye drops are particularly preferable.

Because it is possible to suppress the adsorption of alginic acid and/or a salt thereof to an SCL, the ophthalmic composition of the present invention is preferably used as an ophthalmic composition for an SCL such as an eye drop that can be used while wearing an SCL (an eye drop for an SCL), an eye wash that can be used while wearing an SCL (an eye wash for an SCL), a wetting and rewetting drop for an SCL, or a care solution for an SCL (a disinfecting solution for an SCL, a storage solution for an SCL, a washing solution for an SCL, or a washing and storage solution for an SCL). Any type of SCL can be used; high-water content, ionic SCLs (soft contact lens classification: Group IV) and zwitterionic SCLs are preferable. Proteins easily adsorb to high-water content, ionic SCLs; additionally, if proteins adsorb to an SCL, the adsorption of alginic acid and/or a salt thereof tends to increase. The adsorption of alginic acid and/or a salt thereof to the material for the zwitterionic SCLs is high. However, in the ophthalmic composition of the present invention, the effects of suppressing the adsorption of alginic acid and/or a salt thereof to both of high-water content, ionic SCL and the zwitterionic SCL can be effectively exhibited. The zwitterionic SCL as used herein describes an SCL prepared from a zwitterionic polymer (for example, a polymer having a quaternary ammonium group and a carboxyl group) as a starting material. The soft contact lens classification as used herein refers to an SCL classification based on "With Respect to the Classification of Soft Contact Lenses", defined by the Medical and Pharmaceutical Evaluation Council No. 645, the Ministry of Health, Labour and Welfare (known as the Ministry of Health and Welfare at that time); a notice from a manager of the Evaluation and Control Division of the Pharmaceutical and Medical Safety Bureau, "With Respect to Treatment of Written Material to be Attached upon Filing Application for Approval of Production (Import) of Soft Contact Lenses and Disinfectants for Soft Contact Lenses" dated Mar. 31, 1999; and the SCLs belonging to Group IV in the classification have common characteristics that the water content is 50% or more, and monomers having anions are contained in a moral percentage of 1% by mole or more in monomers constituting the starting material polymers. This classification is based on the classification of soft contact lenses by FDA (U.S. Food and Drug Administration).

The ophthalmic compositions of the present invention are produced according to known methods. For example, the ophthalmic composition may be prepared by a conventional method, for example, adding Component (A), Component (B), and, if necessary, other components to an aqueous solvate such as purified water or saline so as to obtain desired concentrations.

(II) Method for Improving Retention

As described above, the retention of the ophthalmic composition comprising alginic acid and/or a salt thereof on an ocular mucosa can be improved by Component (B). Thus, the present invention further provides a method for improving the retention of an ophthalmic composition on an ocular mucosa, which comprises the step of mixing Component (B) hyaluronic acid and/or a salt thereof with an ophthalmic composition that contains Component (A) alginic acid and/or a salt thereof. In this method, the types and proportions of Component (A) and Component (B), and other blended components and the like are the same as those described in the paragraphs of (I) ophthalmic composition.

Further, based on the improved retention effect, the present invention also provides a method for retaining an ophthalmic composition on an ocular mucosa, comprising a step of applying the ophthalmic composition described in (I) to an ocular mucosa. In this method, a method for applying the ophthalmic composition described in (I) to an ocular mucosa and the applied amount are not particularly limited, and they may be selected depending on the form of the ophthalmic composition. For example, when the ophthalmic composition is an eye drop, an appropriate amount of the eye drop may be applied to an eye; when the ophthalmic composition is an eye wash, an eye may be washed with an appropriate amount of the wash. Also, when the ophthalmic composition is a wetting and rewetting drop for a contact lens or a care agent for a contact lens, an appropriate amount thereof may be contacted with a contact lens, and then the contact lens to which the composition adheres may be put into an eye.

(III) Method for Reducing Adsorption of Alginic Acid and/or Salt Thereof to SCL

As described above, in an ophthalmic composition comprising alginic acid and/or a salt thereof, the adsorption of alginic acid and/or a salt thereof to an SCL can be suppressed by Component (B). Thus, the present invention further provides a method for reducing the adsorption of alginic acid and/or a salt thereof to an SCL, which comprises the step of mixing Component (B) hyaluronic acid and/or a salt thereof with an ophthalmic composition for an SCL that contains Component (A) alginic acid and/or a salt thereof. In this method, the types and proportions of Component (A) and Component (B), other mixed components, the types of an SCL to be a subject, the types of the ophthalmic composition for an SCL and the like are the same as described in the paragraphs of (I) ophthalmic composition.

Furthermore, based on the effect of reducing the adsorption of alginic acid and/or a salt thereof to an SCL, the present invention also provides a method for suppressing the adsorption of alginic acid and/or a salt thereof to an SCL, comprising a step of contacting the ophthalmic composition described in (I) with an SCL. This method is carried out, for example, by contacting the appropriate amount thereof with the SCL if the ophthalmic composition is a wetting and rewetting drop for a contact lens or a care agent for a contact lens. For example, if the ophthalmic composition is a washing solution for an SCL, the method is carried out by washing an SCL with an appropriate amount of the washing solution for an SCL. If the ophthalmic composition is an eye drop for an SCL or an eye wash for an SCL, the method is carried out by applying an appropriate amount of the eye drop for an SCL or the eye wash for an SCL to an eye wearing an SCL.

EXAMPLES

The following Test Examples, Examples and the like illustrate the present invention in more detail, but are not to be construed to limit the scope thereof. In the Examples below, alginic acid derived from *Lessonia nigrescens*, with an M/G ratio of 1.0 to 1.6; and sodium hyaluronate with the average molecular weight of 1,100,000 to 1,600,000 were used.

Test Example 1

Evaluation-1 of Sense of Use

Eye drops (Example 1 and Comparative Examples 1 and 2) were prepared according to the formulation shown in Table 1, and were respectively filled in polyethylene terephthalate vessels for eye drops. The following sense of use test was performed by three monitors with a tendency for dry-eye. Specifically, first, the eye drop of Example 1 and the eye drop of Comparative Example 2 were, respectively, applied to a right eye and a left eye at the same time, and a stickiness comparison evaluation was done at 5 minutes, 15 minutes and 30 minutes after application to the eyes. Next, after sufficient time (1 hour or more), the eye drop of Example 1 and the eye drop of Comparative Example 1 were respectively applied to the right eye and the left eye at the same time, and a stickiness comparison evaluation was done in the same manner as above.

TABLE 1

| Mixed component (Unit: % by weight) | Example 1 | Comparative Example 1 | Comparative Example 2 |
|---|---|---|---|
| Alginic acid | 0.1 | 0.1 | — |
| Sodium hyaluronate | 0.1 | — | 0.1 |
| Boric acid | 1 | 1 | 1 |
| Borax | 0.2 | 0.2 | 0.2 |
| Sodium chloride | 0.4 | 0.4 | 0.4 |
| Purified water | Appropriate amount | Appropriate amount | Appropriate amount |
| Total volume | 100 mL | 100 mL | 100 mL |
| pH | 7.0 | 7.0 | 7.0 |
| Ratio of osmotic pressure | 1.1 | 1.1 | 1.1 |

The results are shown in Table 2. From the results, it was confirmed that the eye drop comprising alginic acid and sodium hyaluronate (Example 1) had reduced stickiness and better sense of use than the eye drop comprising either alginic acid or sodium hyaluronate alone (Comparative Example 1 or 2). The eye drop of Comparative Example 2 caused blurred vision immediately after application to the eyes; however, the eye drop of Example 1 had decreased blurred vision.

TABLE 2

| | | Results of Evaluation (Number of persons) | | |
|---|---|---|---|---|
| | | 5 minutes after application of an eye drop | 15 minutes after application of an eye drop | 30 minutes after application of an eye drop |
| Comparison of Example 1 and Comparative Example 1 | Eye drop of Example 1 has less stickiness than eye drop of Comparative Example 1. | 3 | 2 | 2 |
| | Eye drop of Example 1 has similar stickiness to eye drop of Comparative Example 1. | 0 | 1 | 1 |
| | Eye drop of Example 1 has more stickiness than eye drop of Comparative Example 1. | 0 | 0 | 0 |

TABLE 2-continued

|  |  | Results of Evaluation (Number of persons) | | |
|---|---|---|---|---|
|  |  | 5 minutes after application of an eye drop | 15 minutes after application of an eye drop | 30 minutes after application of an eye drop |
| Comparison of Example 1 and Comparative Example 2 | Eye drop of Example 1 has less stickiness than eye drop of Comparative Example 2. | 3 | 3 | 3 |
|  | Eye drop of Example 1 has similar stickiness to eye drop of Comparative Example 2. | 0 | 0 | 0 |
|  | Eye drop of Example 1 has more stickiness than eye drop of Comparative Example 2. | 0 | 0 | 0 |

Test Example 2

Evaluation-2 of Sense of Use

The eye drop of Example 1 used in Test Example 1 was applied to the eyes of healthy subjects, and the "spreading feeling (feeling that an eye drop is spread over an eye)" and "fit (feeling that an eye drop remains without running off)" after application to the eyes were evaluated. The results found that the eye drop of Example 1 showed better results in "spreading feeling" and "fit" results, and a satisfactory sense of use, which had not been realized in conventional eye drops, could be obtained.

Test Example 3

Gelation Property Test

Ophthalmic compositions (Example 2 and Comparative Example 3) shown in Table 3 were prepared. In order to evaluate the gelation property (gelation property in the presence of calcium ions) of these ophthalmic compositions, the ophthalmic composition of Example 2 or Comparative Example 3 was intentionally turned into a gel, and the strength of the gel was measured.

TABLE 3

| Mixed component (Unit: % by weight) | Example 2 | Comparative Example 3 |
|---|---|---|
| Sodium alginate | 0.5 | 0.5 |
| Sodium hyaluronate | 0.1 | — |
| Boric acid | 1.0 | 1.0 |
| Borax | 0.2 | 0.2 |
| Hydrochloric acid | Appropriate amount | Appropriate amount |
| Sodium hydroxide | Appropriate amount | Appropriate amount |
| Purified water | Appropriate amount | Appropriate amount |
| pH | 7 | 7 |

Specifically, the method for measuring is as follows.

1. Material for Measuring $CaCl_2$.EDTA Solution 7.35 g of calcium chloride dihydrate and 18.6 g of disodium ethylenediamine tetraacetate dihydrate were dissolved in purified water. The solution was adjusted to pH 7.0 to 7.5 with a sodium hydroxide solution, and then was precisely adjusted to 1 L.

GDL Solution 3 mL of water was added to 0.5 g of glucono-d-lactone, produce a solution. The solution was prepared on use.

2. Method for Measuring

To 20 mL of the ophthalmic composition of Example 2 or Comparative Example 3, 9 mL of the $CaCl_2$.EDTA solution and 3 mL of the GDL solution were added, and the mixtures were stirred. The resulting mixed solution was poured into a stainless steel Petri dish having a diameter of 6 cm, and allowed to stand at room temperature for 30 minutes. After a while, the strength of the obtained gel was measured using a Texture Analyser (produced by Stable MicroSystems Ltd.). In this measurement, the probe used was a stainless steel SMSP/1 KS. Specific measuring conditions are as shown in Table 4 below.

TABLE 4

| Test Mode | Compression |
|---|---|
| PreTest Speed | 1.0 mm/sec |
| Test Speed | 2.0 mm/sec |
| Post-Test Speed | 10.0 mm/sec |
| Target Mode | Distance |
| Distance | 3.0 mm |
| Trigger Type | Auto (Force) |
| Trigger Force | 5.0 g |
| Break Mode | Off |
| Stop Plot At | Start Position |
| Trade Mode | Auto |

As a result, it was confirmed that the average strength of the gel of the ophthalmic composition of Comparative Example 3 was 0.01572 $kg/cm^2$, whereas the average strength of the gel of the ophthalmic composition of Example 2 was 0.00939 $kg/cm^2$; the compositions therefore apparently had different gel strength characteristic. In other words, the ophthalmic compositions of Example 2 and Comparative Example 3 were quite different in terms of the physical property of the composition itself. In the gel obtained by mixing the ophthalmic composition of Example 2 or Comparative Example 3, the $CaCl_2$.EDTA solution, and the GDL solution under the same conditions as above, and allowing the mixture to stand at room temperature overnight to sufficiently solidify it, similar to the above, it was discovered that the ophthalmic composition of Example 2 tended to have a lower gelation property than the ophthalmic composition of Comparative Example 3.

Test Example 4

Test for Retention—1

The test for retention was performed using Wistar male rats 200 to 300 g in body weight (Japan SLC Inc.) according to a method outlined below. Each compound was dissolved in a 10 mM phosphoric acid buffer (Kohjin-Bio Incorporated Company) containing 1 w/v % fluorescein to a final concentration shown in Table 5 to prepare a test solution (Example Test Solution 1). Using a micropipetter (Eppendorf Co., Ltd.), 1.0 µl of each test solution was applied to the eye of the rat. One hour after the application, the rat was sacrificed by cervical dislocation, and the eyeball with the bulbar conjunctiva was isolated. The isolated eyeball was soaked in 0.5 ml of a 10 mM phosphoric acid buffer for 24 hours to extract the fluorescein remaining on the surface of the eyeball. The fluorescence intensity (excitation: 480 nm, fluorescence: 527 nm) of each extract was measured using a fluorescence plate reader (Thermo Electron Co., Ltd.). As a background value, using a 10 mM phosphoric acid buffer (Kohjin-Bio Incorporated Company) containing 1 w/v % fluorescein as a test solution, the same test as above was performed, and the fluorescence intensity was measured. The actual value of the fluorescence intensity of Example Test Solution 1 was calculated by subtracting the background value from the fluorescence intensity of Example Test Solution 1. Fluorescein is a substance generally used as an indicator in tests for the capacity of retaining tear fluid and kinetic tests of a water-soluble component (see reference documents such as: Practical Ophthalmology (Ophthalmic Medical Practice) Vol. 4, No. 12, 2001, p 36-39; Br J. Ophthalmol. 2003, April; 87(4): 436-40.; Reference Test Example 1, and the like).

The results showed that the determined fluorescence intensity was 7.9. From this result, it was expected that when both alginic acid and sodium hyaluronate were used, the retention of the composition on an ocular mucosa was remarkably improved compared with Comparative Test Solution 1; therefore, the retention of alginic acid and sodium hyaluronate were remarkably improved.

TABLE 5

| Mixed component (Unit: % by weight) | Test Solution 1 |
|---|---|
| Alginic acid | 0.05 |
| Sodium hyaluronate | 0.05 |

Test Example 5

Test for Retention—2

Each compound was dissolved in a 10 mM phosphoric acid buffer (Kohjin-Bio Incorporated Company) containing 1 w/v % fluorescein to a final concentration shown in Table 6, to prepare each test solution (Example Test Solutions 2 and 3, and Comparative Test Solutions 1 to 3). Using these test solutions, the test was performed in the same manner as in Test Example 4.

The results are shown in FIG. 1. From these results, it was confirmed that, similarly to Example Test Solution 1, Example Test Solutions 2 and 3 had the improved retention on the ocular mucosa of the rats.

TABLE 6

| Mixed component (Unit: % by weight) | Example Test Solution 2 | Example Test Solution 3 | Comparative Test Solution 1 | Comparative Test Solution 2 | Comparative Test Solution 3 |
|---|---|---|---|---|---|
| Alginic acid | 0.05 | 0.05 | 0.05 | — | — |
| Sodium hyaluronate | 0.01 | 0.1 | — | 0.01 | 0.1 |

Test Example 6

Test for Retention—3

Each compound was dissolved in a 10 mM phosphoric acid buffer (Kohjin-Bio Incorporated Company) containing 1 w/v % fluorescein to a final concentration shown in Table 7 to prepare a test solution (Example Test Solution 4). Using this test solution, the test for retention was performed in the same manner as in Test Example 4. From this result, it was confirmed that, similarly to the cases of Example Test Solutions 1 to 3, Example Test Solution 4 had improved retention on the ocular mucosa of the rat, compared to Comparative Test Solution 1.

TABLE 7

| Mixed component (Unit: % by weight) | Example Test Solution 4 |
|---|---|
| Alginic acid | 0.05 |
| Sodium hyaluronate | 0.05 |

Overall Review of Test Examples 1 to 6

The results of Test Examples 4 to 6 showed that when alginic acid and/or a salt thereof and hyaluronic acid and/or a salt thereof were used together, the retention of the compositions on ocular mucosa was remarkably improved. These results suggest that when another pharmacologically active ingredient was mixed with the ophthalmic composition of the present invention, the resulting composition could have improved retention of the pharmacologically active ingredient on the ocular mucosa. Such an improvement in the retention of the pharmacologically active ingredient on the ocular mucosa is useful for the alleviation or amelioration of symptoms such as corneal drying and inflammation, which often occur in contact lens users; accordingly, the ophthalmic composition of the present invention was revealed to be useful as the ophthalmic composition for an SCL.

From the results of Test Examples 1 to 6, it was revealed that the ophthalmic composition of the present invention has reduced gelation properties compared with the ophthalmic composition comprising alginic acid and/or a salt thereof alone, different physical properties from the composition itself, as well as a difference in sense of use. Generally, it is thought that the greater the gelation property, the better the retention of an ophthalmic composition on an ocular mucosa. However, although the ophthalmic composition of the present invention has a lower gelation property than the composition comprising alginic acid and/or a salt thereof alone, it has improved retention on an ocular mucosa, and is therefore very useful.

Test Example 7

Test for Evaluating Suppression in Adsorption of Alginic Acid to SCL

The following test was performed to examine the effects of sodium hyaluronate on the adsorption of alginic acid to an SCL.

Materials for Test

The ophthalmic compositions shown in Table 8 (Example 3 and Comparative Example 4) were prepared by a conventional method. In this test, as an SCL, "Seed 2 Week Pure" (trade name; a zwitterionic produced by Seed Co., Ltd.: hydrous; component monomers: hydroxyethyl methacrylate (HEMA), quaternary ammonium group-containing methacrylate compounds, carboxyl group-containing methacrylate compounds, methyl methacrylate (MMA), and ethylene glycol dimethacrylate (EGDMA); soft contact lens classification: Group IV) was used.

Test Method

Each SCL was soaked in 5 mL of saline according to the Japanese Pharmacopoeia, and allowed to stand for about 24 hours at room temperature (about 25° C.). The SCL was then taken out of the saline, and the moisture was wiped off gently. 4 mL of each of the ophthalmic compositions of Example 3 and Comparative Example 4 was added to a highly hermetic and transparent glass vial. The two SCLs obtained above were soaked in each of the ophthalmic compositions, which were shaken at a frequency of 120 rotations/minute at a temperature of 34° C. for about 72 hours, after which the SCLs were taken out. Next, the concentration of alginic acid remaining in each of the ophthalmic compositions after soaking the SCL (hereinafter referred to as an Alg concentration after the test) was measured using a high-performance liquid chromatograph. A blank test was carried out in the same manner as above, except that an SCL was not soaked, and the concentration of alginic acid remaining in the ophthalmic composition when the SCL was not soaked (hereinafter referred to as a blank Alg concentration) was measured.

From the measured concentrations of alginic acid, an amount of adsorbed alginic acid (µg/SCL) was calculated and a percentage of suppressing the adsorption of alginic acid (%) was determined in accordance with the following equations.

Amount of adsorbed alginic acid (µg/SCL)=(blank Alg concentration (µg/mL)−Alg concentration after the test (µg/mL))/2(number of SCL)

Percentage of suppressed adsorption of alginic acid (%)={1−(amount of adsorbed alginic acid of Example/amount of adsorbed alginic acid of Comparative Example)}×100  [Equation 1]

The results are collectively shown in Table 8. In the ophthalmic composition of Comparative Example 4, alginic acid adsorbed to the SCL. Comparatively, in the ophthalmic composition of Example 3, in which sodium hyaluronate is mixed, the adsorption of alginic acid to an SCL was suppressed.

TABLE 8

| Mixed component (% by weight) | Example 3 | Comparative Example 4 |
|---|---|---|
| Alginic acid | 0.05 | 0.05 |
| Sodium chloride | 0.44 | 0.44 |
| Potassium chloride | 0.08 | 0.08 |
| Boric acid | 1 | 1 |
| Borax | 0.2 | 0.2 |
| Sodium hyaluronate | 0.005 | — |
| Hydrochloric acid | Appropriate amount | Appropriate amount |
| Sodium hydroxide | Appropriate amount | Appropriate amount |
| Purified water | Appropriate amount | Appropriate amount |
| Total volume | 100 mL | 100 mL |
| pH | 7.2 | 7.2 |
| Ratio of suppressed adsorption (%) | 100 | — |

Test Example 5

Test for Evaluating Suppression in Adsorption of Alginic Acid to SCL—3

In order to examine the effect of potassium aspartate, aminoethylsulfonic acid, sodium chondroitin sulfate, or sodium hyaluronate on the adsorption of alginic acid to an SCL to which a protein adheres, the following test was performed.

<Materials for Test>

Ophthalmic compositions for SCLs shown in Table 9 (Example 4 and Comparative Example 5) were prepared by a conventional method. In this test, as an SCL, the following lenses were used.

A: "Medalist Plus" (trade name; produced by Bausch & Lomb Company Ltd., hydrous, main component: hydroxyethyl methacrylate (HEMA), soft contact lens classification: Group I)

B: "2 Week Acuvue" (trade name; produced by Johnson & Johnson K.K., hydrous, main component: a copolymer of hydroxyethyl methacrylate (HEMA) and methacrylic acid (MAA))

<Test Method>

1.0 g of ovalbumin, 0.1 g of lysozyme chloride, and 0.1 g of porcine gastric mucin were weighed and were dissolved in 100 mL of a phosphoric acid buffer (see Japanese Pharmacopoeia Fifteenth Edition, General Test Procedures, Phosphate buffer, pH 7.2) to produce an artificial stain solution having a pH of 7.2. The unused test contact lens described above was soaked in 5 mL of this solution, which was shaken at 37° C. for about 8 hours. After that, each lens was taken out of the artificial stain solution and lightly rinsed with saline to remove excessive artificial stain solution, after which the moisture was wiped off gently. Then, 4 ml of each of the ophthalmic compositions for SCLs of Example 4 and Comparative Example 5 was added to a highly hermetic and transparent glass vial, and the two SCLs obtained above were soaked in each of the ophthalmic compositions for SCLs, which was shaken at a frequency of 120 rotations/minute at a temperature of 34° C. for about 72 hours, after which the SCLs was taken out. Next, the concentration of alginic acid remaining in each of the ophthalmic compositions after soaking the SCL (Alg concentration after the test) was measured using a high-performance liquid chromatograph. A blank test was carried out in the same manner as above, except that an SCL was not soaked, and a concentration of alginic acid remaining in the ophthalmic composition in the case where the SCL was not soaked (blank Alg concentration) was measured.

From the measured concentrations of alginic acid, an amount of the adsorbed alginic acid (μg/SCL) was calculated and a percentage of the reduced adsorption of alginic acid (%) was determined in accordance with the equations shown in Equation 1 described above.

TABLE 9

| Mixed component (% by weight) | Example 4 | Comparative Example 5 |
|---|---|---|
| Alginic acid | 0.05 | 0.05 |
| Sodium Chloride | 0.6 | 0.6 |
| Boric acid | 0.8 | 0.8 |
| Borax | 0.15 | 0.15 |
| Sodium hyaluronate | 0.01 | — |
| Hydrochloric acid | Appropriate amount | Appropriate amount |
| Sodium hydroxide | Appropriate amount | Appropriate amount |
| Purified water | Appropriate amount | Appropriate amount |
| Total Volume | 100 mL | 100 mL |
| pH | 7.0 | 7.0 |
| Ratio of suppressed adsorption to lens A (%) | 75 | — |
| Ratio of suppressed adsorption to lens B (%) | 100 | — |

The results are collectively shown in Table 9. In the ophthalmic composition for an SCL of Comparative Example 5, alginic acid adsorbed to an SCL. Comparatively, it was found that in the ophthalmic composition of Example 4, in which sodium hyaluronate is comprised, the adsorption of alginic acid to an SCL was remarkably reduced.

Reference Test Example 1

FIG. 2 shows the results obtained by applying saline containing 0.001 w/v % fluorescein, or saline containing 0.001 w/v % fluorescein and 0.2 w/v % alginic acid to the eyes of domestic rabbits, measuring the fluorescence intensity on the anterior ocular segment over time using a fluorometer, and comparing them. The fluorescence intensities in the saline rapidly decreased, whereas those in the saline containing alginic acid did not show a significant decrease in the fluorescence intensity. From these results, it might be considered that alginic acid facilitates the retention of a substance dissolved in an eye drop.

Next, saline containing 0.25 w/v % timolol, which has an ocular hypotensive effect, or saline containing 0.25 w/v % timolol and 0.2 w/v % sodium alginate was applied to eyes of domestic rabbits, eye pressures were measured over time, and the retentions of the effect were compared. The results are shown in FIG. 3. The eye pressure in the case of applying the saline containing 0.25 w/v % timolol returned to the original eye pressure after about 5 hours, whereas that in the case of applying the saline containing 0.25 w/v % timolol and 0.2 w/v % sodium alginate returned to the original pressure after about 8 hours, and the retention of the ocular hypotensive effect was apparently observed.

From the results in FIG. 2, it might be considered that in the saline containing 0.25% timolol, the timolol disappeared from the saccus conjunctivae within 1 hour after application to the eyes, whereas in the saline containing 0.25 w/v % timolol and 0.2 w/v % sodium alginate, the timolol remained on the saccus conjunctivae even after 1 hour. It might be considered that at a result, timolol was persistently absorbed to the eye, and the cumulative amount of adsorption was increased, thus resulting in sustentation of the ocular hypotensive effect.

Formulation Examples

According to the formulations shown in Tables 10 to 12, eye drops (Examples 5 to 13), artificial tear fluid type eye drops (Examples 14 to 18), eye drops for SCLs (Examples 19 to 24, 41 and 42), eye washes (Examples 25 to 32), wetting and rewetting drops for SCLs (Examples 33 and 34), eye washes for SCLs (Examples 35 and 36), storage agents for SCLs (Examples 37 and 38), and disinfectants for SCLs (Examples 39 and 40) were prepared.

TABLE 10

| Combined component (Unit: % by weight) | Example | | | | | | | | | | |
|---|---|---|---|---|---|---|---|---|---|---|---|
| | 5 | 6 | 7 | 8 | 9 | 10 | 11 | 12 | 13 | 14 | 15 |
| Alginic acid | 0.05 | 0.05 | 0.01 | 0.2 | 0.05 | 0.1 | 0.005 | — | — | 0.05 | — |
| Sodium alginate | — | — | — | — | — | — | — | 0.05 | 0.05 | — | 0.05 |
| Sodium hyaluronate | 0.05 | 0.05 | 0.02 | 0.06 | 0.05 | 0.05 | 0.01 | 0.1 | 0.08 | 0.03 | 0.03 |
| Sodium cromoglycate | 1 | 1 | 1 | 1 | — | — | — | — | — | — | — |
| Tetrahydrozoline hydrochloride | — | — | — | — | — | — | 0.05 | — | — | — | — |
| Naphazoline hydrochloride | — | — | — | — | — | — | — | — | 0.003 | — | — |
| Neostigmine methylsulfate | — | — | — | — | — | — | 0.005 | — | 0.005 | — | — |
| Chlorpheniramine maleate | 0.015 | 0.015 | 0.015 | 0.015 | 0.03 | 0.01 | 0.03 | 0.03 | 0.03 | — | — |
| Sodium azulene sulfonate | — | — | — | — | 0.02 | — | — | — | — | — | — |
| Berberine sulfate | — | — | — | — | — | — | — | — | — | — | — |
| Dipotassium glycyrrhizinate | 0.1 | — | — | — | 0.1 | — | — | 0.25 | 0.1 | — | — |
| Pyridoxine hydrochloride | 0.05 | — | 0.1 | 0.1 | 0.05 | 0.1 | 0.1 | 0.1 | 0.1 | — | — |
| Cyanocobalamine | — | — | — | — | — | 0.01 | — | — | — | — | — |
| L-aspartate potassium salt | 0.5 | — | 1 | 0.5 | 0.5 | 1 | 1 | 0.5 | 1 | — | — |
| Aminoethylsulfonic acid | 0.5 | — | — | — | 0.5 | — | — | 0.1 | 1 | — | — |
| Sodium chondroitin sulfate | 0.1 | — | 0.1 | 0.5 | 0.1 | 0.1 | — | 0.1 | 0.5 | 0.5 | 0.5 |
| Hydroxyethyl cellulose (FUJI CHEMI CF-V) | — | — | — | — | — | — | 0.1 | 0.5 | — | — | — |
| Hydroxypropyl methylcellulose (METOLOSE 65SH-4000) | — | — | — | — | — | — | — | — | — | 0.01 | 0.4 |
| Hydroxypropyl methylcellulose (METOLOSE 60SH-4000) | — | — | — | — | — | — | — | — | 0.5 | — | — |
| Hydroxypropyl methylcellulose (METOLOSE 90SH-4000) | 0.5 | — | — | — | 0.5 | — | — | — | — | — | — |
| Polyvinyl alcohol (GOSENOL EG-05) | — | 0.5 | — | — | — | — | — | — | — | — | — |

TABLE 10-continued

| | | | | | | | | | | | |
|---|---|---|---|---|---|---|---|---|---|---|---|
| Polyvinylpyrrolidone (PVP K25) | — | — | 1 | — | — | 1 | — | — | — | — | — |
| Polyvinylpyrrolidone (PVP K90) | — | — | — | 1 | — | — | — | — | — | — | — |
| l-menthol | 0.01 | 0.005 | 0.005 | 0.002 | 0.01 | 0.005 | 0.01 | 0.005 | 0.02 | 0.002 | 0.003 |
| d-camphor | 0.005 | 0.005 | 0.002 | — | 0.005 | 0.002 | 0.005 | 0.001 | 0.01 | 0.005 | 0.001 |
| d-borneol | — | — | — | — | — | — | 0.005 | — | — | — | — |
| Geraniol | — | — | — | 0.002 | — | — | — | — | 0.002 | 0.001 | — |
| Menthone | — | — | — | — | — | 0.0001 | — | — | — | 0.001 | — |
| Linalyl acetate | — | — | — | — | 0.0001 | — | — | — | — | 0.001 | — |
| Cineole | — | — | — | — | — | — | — | — | 0.001 | 0.005 | — |
| Bergamot oil | — | — | — | — | — | — | — | — | — | — | — |
| Polyoxyethylene hydrogenated castor oil 60 | — | 0.1 | 0.1 | 0.1 | — | 0.1 | 0.5 | — | 0.2 | — | — |
| Polysorbate 80 | 0.2 | — | 0.1 | — | 0.2 | 0.1 | — | 0.5 | — | 0.05 | 0.05 |
| Poloxamer 407 | — | — | — | 0.1 | — | — | — | — | 0.05 | 0.05 | 0.05 |
| Glucose | — | — | — | — | — | — | — | — | — | — | 0.09 |
| Potassium chloride | — | — | — | — | — | — | — | — | — | 0.08 | 0.08 |
| Calcium chloride | — | — | — | — | — | — | — | — | — | 0.005 | — |
| Sodium chloride | — | — | — | — | — | — | — | — | — | q.s. | q.s. |
| Sodium hydrogen carbonate | — | — | — | — | — | — | — | — | — | 0.05 | — |
| Boric acid | 1 | — | 1 | 0.8 | 1 | 1 | 1 | 1 | 0.8 | 1 | 1 |
| Borax | 0.3 | — | 0.01 | 0.01 | 0.3 | 0.01 | 0.25 | 0.05 | 0.005 | 0.22 | 0.14 |
| Sodium hydrogenphosphate | — | 1.22 | — | — | — | — | — | — | — | — | — |
| Sodium dihydrogen phosphate | — | 0.22 | — | — | — | — | — | — | — | — | — |
| Sodium edetate | — | — | — | — | — | — | — | — | — | 0.05 | 0.05 |
| Chlorobutanol | — | — | 0.02 | 0.1 | — | 0.02 | 0.01 | 0.1 | — | — | — |
| Trometamol | — | — | — | — | — | — | — | — | — | — | — |
| Hydrochloric acid | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. |
| Purified water | q.s. | q.s. | q.s. | q.s. | q.s. | q.s. | q.s. | q.s. | q.s. | q.s. | q.s. |
| Total volume | 100 mL | 100 mL | 100 mL | 100 mL | 100 mL | 100 mL | 100 mL | 100 mL | 100 mL | 100 mL | 100 mL |
| pH | 7.5 | 7.2 | 5.5 | 5 | 7.5 | 5.5 | 7 | 5.5 | 5.5 | 7 | 7.2 |

| Combined component | Example | | | | | | | | |
|---|---|---|---|---|---|---|---|---|---|
| (Unit: % by weight) | 16 | 17 | 18 | 19 | 20 | 21 | 22 | 23 | 24 |
| Alginic acid | 0.05 | 0.05 | 0.1 | 0.05 | — | 0.1 | 0.1 | 0.1 | 0.05 |
| Sodium alginate | — | — | — | — | 0.1 | — | — | — | — |
| Sodium hyaluronate | 0.02 | 0.05 | 0.01 | 0.01 | 0.05 | 0.01 | 0.01 | 0.01 | 0.01 |
| Sodium cromoglycate | — | — | — | — | — | — | — | — | — |
| Tetrahydrozoline hydrochloride | — | — | — | — | — | — | — | — | — |
| Naphazoline hydrochloride | — | — | — | — | — | — | — | — | — |
| Neostigmine methylsulfate | — | — | — | — | — | — | — | — | — |
| Chlorpheniramine maleate | — | — | — | — | — | — | — | — | — |
| Sodium azulene sulfonate | — | — | — | — | — | — | — | — | — |
| Berberine sulfate | — | — | — | — | — | — | — | — | — |
| Dipotassium glycyrrhizinate | — | — | — | — | — | — | — | — | — |
| Pyridoxine hydrochloride | — | — | — | — | — | — | 0.01 | — | — |
| Cyanocobalamine | — | — | — | — | — | — | — | — | — |
| L-aspartate potassium salt | — | — | 0.5 | 0.5 | 0.1 | 0.5 | 0.5 | 0.5 | 0.5 |
| Aminoethylsulfonic acid | — | — | 0.5 | 0.5 | 1 | 0.5 | 0.5 | 0.5 | 0.5 |
| Sodium chondroitin sulfate | 0.5 | 0.5 | 0.5 | 0.5 | 0.05 | 0.5 | 0.5 | 0.5 | 0.5 |
| Hydroxyethyl cellulose (FUJI CHEMI CF-V) | — | — | — | — | — | — | — | — | — |
| Hydroxypropyl methylcellulose (METOLOSE 65SH-4000) | 0.01 | 0.4 | 0.05 | 0.05 | 0.25 | 0.4 | 0.25 | 0.05 | 0.05 |
| Hydroxypropyl methylcellulose (METOLOSE 60SH-4000) | — | — | — | — | — | — | — | — | — |
| Hydroxypropyl methylcellulose (METOLOSE 90SH-4000) | — | — | — | — | — | — | — | — | — |
| Polyvinyl alcohol (GOSENOL EG-05) | — | — | — | — | 2 | 2 | 2 | — | — |
| Polyvinylpyrrolidone (PVP K25) | — | — | — | — | — | — | — | — | — |
| Polyvinylpyrrolidone (PVP K90) | — | — | — | — | — | — | — | — | — |
| l-menthol | 0.002 | 0.003 | 0.015 | 0.005 | 0.005 | 0.005 | 0.005 | 0.015 | 0.005 |
| d-camphor | 0.005 | 0.001 | 0.005 | 0.001 | — | — | — | 0.005 | 0.001 |
| d-borneol | — | — | — | — | — | — | — | — | — |
| Geraniol | 0.001 | — | 0.001 | — | — | 0.005 | — | 0.001 | — |
| Menthone | 0.001 | — | — | — | — | — | — | — | — |
| Linalyl acetate | 0.001 | — | — | — | — | — | — | — | — |
| Cineole | 0.005 | — | — | — | — | — | — | — | — |
| Bergamot oil | — | — | — | — | — | — | 0.002 | — | — |
| Polyoxyethylene hydrogenated castor oil 60 | — | — | — | — | 0.05 | 0.05 | 0.05 | — | — |
| Polysorbate 80 | 0.05 | 0.05 | 0.05 | 0.05 | — | — | — | 0.05 | 0.05 |

TABLE 10-continued

|  |  |  |  |  |  |  |  |  |  |
|---|---|---|---|---|---|---|---|---|---|
| Poloxamer 407 | 0.05 | 0.05 | 0.05 | 0.05 | — | 0.05 | 0.05 | 0.05 | 0.05 |
| Glucose | — | 0.09 | — | — | — | — | — | — | — |
| Potassium chloride | 0.08 | 0.08 | 0.08 | 0.08 | 0.08 | 0.08 | 0.08 | 0.08 | 0.08 |
| Calcium chloride | 0.005 | — | — | — | — | — | — | — | — |
| Sodium chloride | — | — | — | — | q.s. | q.s. | q.s. | — | — |
| Sodium hydrogen carbonate | 0.05 | — | — | — | — | — | — | — | — |
| Boric acid | 1 | 1 | 0.8 | 0.8 | — | — | — | 0.8 | 0.8 |
| Borax | 0.22 | 0.14 | 0.1 | 0.1 | — | — | — | 0.1 | 0.1 |
| Sodium hydrogenphosphate | — | — | — | — | — | 0.2 | 0.2 | — | — |
| Sodium dihydrogen phosphate | — | — | — | — | — | 0.04 | 0.04 | — | — |
| Sodium edetate | 0.05 | 0.05 | 0.05 | 0.05 | 0.1 | 0.05 | 0.05 | 0.05 | 0.05 |
| Chlorobutanol | — | — | — | — | — | — | — | — | — |
| Trometamol | — | — | — | — | 0.5 | — | — | — | — |
| Hydrochloric acid | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. |
| Purified water | q.s. | q.s. | q.s. | q.s. | q.s. | q.s. | q.s. | q.s. | q.s. |
| Total volume | 100 mL | 100 mL | 100 mL | 100 mL | 100 mL | 100 mL | 100 mL | 100 mL | 100 mL |
| pH | 7 | 7.2 | 6.8 | 7 | 6.6 | 7 | 7 | 6.8 | 7 |

TABLE 11

| Combined component | Example | | | | | | | |
|---|---|---|---|---|---|---|---|---|
| (Unit: % by weight) | 25 | 26 | 27 | 28 | 29 | 30 | 31 | 32 |
| Alginic acid | 0.05 | 0.01 | 0.05 | 0.01 | 0.005 | 0.1 | — | — |
| Sodium alginate | — | — | — | — | — | — | 0.05 | 0.02 |
| Sodium hyaluronate | 0.01 | 0.001 | 0.05 | 0.01 | 0.01 | 0.01 | 0.02 | 0.03 |
| Chlorpheniramine maleate | 0.003 | 0.001 | 0.003 | 0.001 | 0.003 | 0.001 | 0.003 | 0.0006 |
| Dipotassium glycyrrhizinate | 0.01 | — | 0.01 | — | 0.01 | — | — | 0.015 |
| Pyridoxine hydrochloride | 0.005 | 0.01 | 0.005 | 0.01 | 0.005 | 0.01 | 0.01 | 0.01 |
| Tocopherol acetate | — | — | — | — | — | — | — | 0.005 |
| L-potassium aspartate | 0.05 | 0.1 | 0.05 | 0.1 | 0.05 | 0.1 | 0.05 | 0.05 |
| Aminoethylsulfonic acid | 0.05 | — | 0.05 | — | 0.05 | — | — | — |
| Sodium chondroitin sulfate | — | 0.01 | — | 0.01 | — | 0.01 | — | — |
| Hydroxyethyl cellulose (FUJI CHEMI CF-V) | — | — | 0.5 | — | — | — | — | 0.2 |
| Hydroxypropyl methylcellulose (METOLOSE 90SH-4000) | — | — | — | — | 0.5 | — | — | — |
| Polyvinylpyrrolidone (PVP K25) | — | — | — | 1 | — | 1 | — | — |
| l-menthol | 0.01 | 0.005 | 0.01 | 0.005 | 0.01 | 0.005 | 0.001 | 0.002 |
| d-camphor | 0.005 | 0.002 | 0.005 | 0.002 | 0.005 | 0.002 | — | 0.005 |
| d-borneol | — | — | — | — | — | — | — | 0.002 |
| Geraniol | — | — | — | — | — | 0.0001 | — | 0.002 |
| Menthone | — | 0.0001 | — | 0.0001 | — | — | — | — |
| Cineole | 0.001 | — | — | — | — | — | — | — |
| Polyoxyethylene hydrogenated castor oil 60 | — | 0.1 | 0.2 | 0.1 | — | 0.1 | — | 0.2 |
| Polysorbate 80 | 0.2 | 0.1 | — | 0.1 | 0.2 | 0.1 | 0.005 | — |
| Boric acid | 1.7 | 1.5 | 1.7 | 1.5 | 1.7 | 1.5 | 1.5 | 1.5 |
| Borax | 0.35 | 0.35 | 0.35 | 0.35 | 0.35 | 0.35 | 0.35 | 0.05 |
| Sodium edetate | — | — | — | — | — | — | — | 0.02 |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Purified water | q.s. | q.s. | q.s. | q.s. | q.s. | q.s. | q.s. | q.s. |
| Total volume | 100 mL | 100 mL | 100 mL | 100 mL | 100 mL | 100 mL | 100 mL | 100 mL |
| pH | 7.5 | 7.3 | 7.5 | 7.3 | 7.5 | 7.3 | 7.3 | 6.5 |

TABLE 12

| Combined component | Example | | | | | | | | | |
|---|---|---|---|---|---|---|---|---|---|---|
| (Unit: % by weight) | 33 | 34 | 35 | 36 | 37 | 38 | 39 | 40 | 41 | 42 |
| Alginic acid | 0.1 | — | 0.005 | — | 0.15 | — | 0.03 | — | 0.03 | — |
| Sodium alginate | — | 0.005 | — | 0.1 | — | 0.02 | — | 0.2 | — | 0.2 |
| Sodium hyaluronate | 0.01 | 0.002 | 0.005 | 0.03 | 0.005 | 0.015 | 0.06 | 0.1 | 0.06 | 0.1 |
| L-potassium aspartate | — | 0.1 | 0.5 | 1.0 | 0.5 | 0.5 | 0.5 | 0.5 | — | 0.2 |
| Aminoethylsulfonic acid | — | 1 | 0.5 | 0.5 | 0.5 | 0.5 | 0.5 | 0.5 | — | 0.2 |
| Sodium chondroitin sulfate | — | 0.05 | 0.5 | 0.5 | 0.5 | 0.1 | 0.5 | 0.5 | — | 0.5 |
| Hydroxyethyl cellulose (FUJI CHEMI CF-V) | — | — | 0.1 | — | 0.02 | 0.005 | 0.02 | 0.005 | — | 0.005 |

TABLE 12-continued

| Combined component (Unit: % by weight) | Example | | | | | | | | | |
|---|---|---|---|---|---|---|---|---|---|---|
| | 33 | 34 | 35 | 36 | 37 | 38 | 39 | 40 | 41 | 42 |
| Hydroxypropyl methylcellulose (METOLOSE 65SH-4000) | 0.05 | — | — | — | 0.05 | — | 0.05 | — | 0.05 | — |
| Hydroxypropyl methylcellulose (METOLOSE 60SH-4000) | — | 0.25 | — | — | — | — | — | — | — | — |
| Polyvinyl alcohol (GOSENOL EG-05) | 2 | — | — | — | — | — | — | — | — | — |
| Polyvinylpyrrolidone (PVP K25) | — | 0.1 | — | — | — | — | — | — | — | — |
| l-menthol | — | 0.001 | — | 0.005 | — | 0.015 | — | 0.015 | — | — |
| d-camphor | — | 0.005 | — | — | — | — | — | — | — | — |
| d-borneol | — | — | — | 0.002 | — | — | — | — | — | — |
| Geraniol | — | — | 0.005 | — | 0.001 | — | 0.001 | — | — | — |
| Bergamot oil | — | — | — | 0.002 | — | — | — | — | — | — |
| Polyoxyethylene hydrogenated castor oil 60 | — | 0.02 | — | 0.1 | 0.2 | — | — | — | — | — |
| Polysorbate 80 | 0.1 | — | 0.2 | — | — | 0.05 | 0.2 | 0.05 | 0.2 | — |
| Poloxamer 407 | 0.05 | — | — | 0.05 | 0.05 | — | 0.05 | — | 0.05 | 0.05 |
| Glucose | — | — | 0.1 | — | — | — | — | — | — | — |
| Potassium chloride | — | 0.08 | — | 0.08 | — | 0.08 | — | 0.08 | — | 0.08 |
| Sodium chloride | 0.44 | 0.44 | 0.6 | 0.7 | 0.3 | 0.6 | 0.3 | 0.6 | 0.3 | 0.6 |
| Sodium hydrogen carbonate | — | 0.05 | — | — | — | — | — | — | — | — |
| Boric acid | 0.8 | — | 1.5 | — | 0.8 | — | 0.8 | 0.8 | 1.0 | 0.8 |
| Borax | 0.1 | — | 0.3 | — | 0.1 | — | 0.1 | 0.1 | 0.2 | 0.1 |
| Sodium hydrogenphosphate | — | 1 | — | 0.5 | — | 0.2 | — | — | — | — |
| Sodium dihydrogen phosphate | — | 0.2 | — | 0.03 | — | 0.04 | — | — | — | — |
| Glycerin | — | — | — | — | 5 | — | — | — | — | — |
| Sodium edetate | — | 0.1 | 0.05 | 0.005 | 0.001 | 0.02 | 0.001 | 0.02 | 0.001 | 0.02 |
| Potassium sorbate | — | 0.1 | — | — | — | — | — | — | — | — |
| Polyhexamethylene biguanide hydrochloride | 0.0003 | — | — | — | — | — | 0.0001 | 0.00005 | — | — |
| Hydrochloric acid | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. |
| Purified water | q.s. | q.s. | q.s. | q.s. | q.s. | q.s. | q.s. | q.s. | q.s. | q.s. |
| Total volume | 100 mL | 100 mL | 100 mL | 100 mL | 100 mL | 100 mL | 100 mL | 100 mL | 100 mL | 100 mL |
| pH | 7 | 6.6 | 7 | 7 | 6.8 | 7 | 6.8 | 7 | 6.8 | 7 |
| Hyaluronic acid/alginic acid × 100 | 10 | 40 | 100 | 30 | 33.333 | 75 | 200 | 50 | 200 | 50 |

BRIEF DESCRIPTION OF THE DRAWINGS

FIG. 3—Figure represents the results obtained in Reference Test 1. That is, the results were obtained by applying saline containing 0.25 w/v % timolol or saline containing 0.25 w/v % timolol and 0.2 w/v % sodium alginate to eyes of domestic rabbits, and measuring the eye pressure over time.

Figure 1:
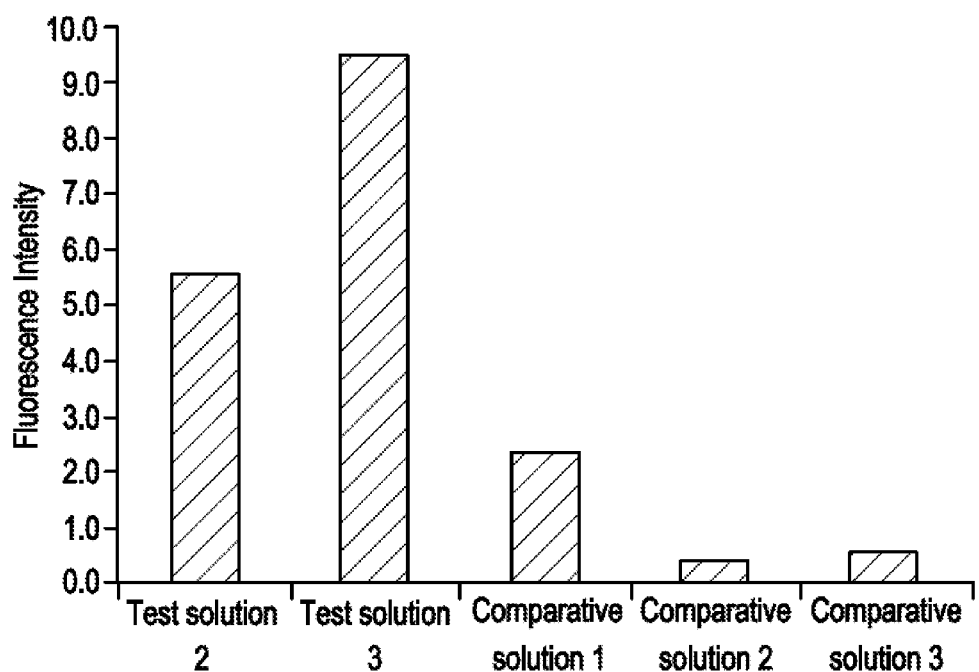
FIG. 1—Figure represents the results of test for the retention of each test solution on an ocular mucosa of a rat in Test Example 5.
Figure 2:
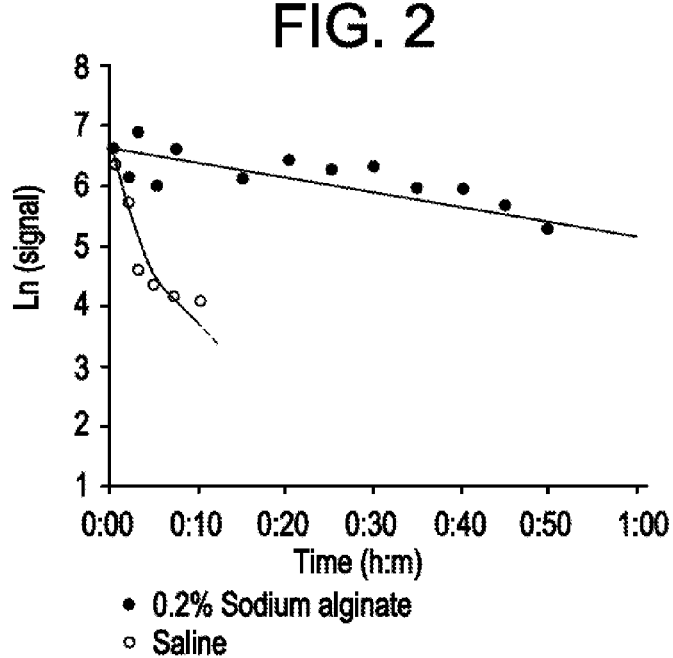
FIG. 2—Figure represents the results obtained in Reference Test Example 1. The results were obtained by applying saline containing 0.001 w/v % fluorescein or saline containing 0.001 w/v % fluorescein and 0.2 w/v % alginic acid to eyes of domestic rabbits, and measuring the fluorescence intensity on the anterior ocular segment over time using a fluorometer.

The invention claimed is:

1. A method for treating dryness or inflammation, or both, in an eye of a subject which comprises applying a therapeutically effective amount of an ophthalmic composition to an eye of a subject in need thereof, wherein the ophthalmic composition comprises 0.001 to 0.1% by weight hyaluronic acid or salts thereof and 0.001 to 0.5% by weight alginic acid or salts thereof, wherein the hyaluronic acid or salts thereof is present at a ratio of 0.3 to 20 parts by weight per 100 parts by weight of the alginic acid or salts thereof, thereby treating dryness or inflammation, or both, in an eye of a subject.

2. The method for treating dryness or inflammation, or both, in an eye of a subject of claim 1, wherein the subject is wearing a soft contact lens on the eye during application of the ophthalmic composition.

* * * * *